US006517679B1

(12) United States Patent
Mustonen et al.

(10) Patent No.: US 6,517,679 B1
(45) Date of Patent: Feb. 11, 2003

(54) METHOD FOR DETERMINATION OF AN IRREVERSIBLE STRETCH AND OF A DYNAMIC MODULUS OF ELASTICITY

(75) Inventors: Harri Mustonen, Jyväskylä (FI); Pekka Pakarinen, Jyväskylä (FI); Mika Tammenoja, Jyväskylä (FI)

(73) Assignee: Metso Paper, Inc., Helsinki (FI)

( * ) Notice: Subject to any disclaimer, the term of this patent is extended or adjusted under 35 U.S.C. 154(b) by 0 days.

(21) Appl. No.: 09/623,205

(22) PCT Filed: Feb. 22, 1999

(86) PCT No.: PCT/FI99/00138

§ 371 (c)(1),
(2), (4) Date: Aug. 25, 2000

(87) PCT Pub. No.: WO99/44058

PCT Pub. Date: Sep. 2, 1999

(30) Foreign Application Priority Data

Feb. 25, 1998 (FI) .................................................. 980428

(51) Int. Cl.[7] .......................... G01N 33/34; G01N 3/08; B65H 77/00; D21F 7/06
(52) U.S. Cl. .............................. 162/198; D62/DIG. 11; 700/128; 73/73; 73/760; 73/781; 73/159
(58) Field of Search ........................ 162/198, 49, 263, 162/DIG. 6, DIG. 10, DIG. 11; 700/127–129; 73/73, 296, 760, 781, 795, 862.454, 159.37

(56) References Cited

U.S. PATENT DOCUMENTS

| 2,755,032 A | 7/1956 | Justus | 242/75 |
|---|---|---|---|
| 3,057,574 A | 10/1962 | Justus | 242/75.43 |
| 3,718,037 A | 2/1973 | Stringer et al. | 73/144 |
| 3,933,035 A | 1/1976 | Roch | 73/95.5 |
| 4,866,984 A | 9/1989 | Houghton | 73/159 |
| 5,013,403 A | * 5/1991 | Chase | 162/49 |
| 5,026,458 A | * 6/1991 | Beuther | 162/198 |
| 5,029,469 A | * 7/1991 | Chase et al. | 73/159 |
| 5,104,488 A | * 4/1992 | Chase | 162/198 |
| 5,269,883 A | * 12/1993 | Beuther | 162/198 |
| 5,649,448 A | 7/1997 | Koskimies et al. | 73/159 |
| 5,658,432 A | * 8/1997 | Heaven et al. | 162/198 |
| 5,891,306 A | * 4/1999 | Chase et al. | 162/198 |

FOREIGN PATENT DOCUMENTS

| EP | 0311507 | 4/1989 |
|---|---|---|
| EP | 0826821 | 3/1998 |
| FI | 62419 | 8/1980 |
| FI | 80522 | 2/1990 |
| GB | 2281632 | 3/1995 |

* cited by examiner

*Primary Examiner*—José Fortuna
(74) *Attorney, Agent, or Firm*—Steinberg & Raskin, P.C.

(57) ABSTRACT

The invention concerns a method for determination of an irreversible stretch and of a dynamic modulus of elasticity from a paper web (W). In the method, the irreversible stretch and the dynamic modulus of elasticity are determined from h paper web (W) by means of on-line measurement. The invention also concerns a method in which the quantities that have been determined are employed in the control of the papermaking process.

8 Claims, 4 Drawing Sheets

METHOD FOR DETERMINATION OF AN IRREVERSIBLE STRETCH AND OF A DYNAMIC MODULUS OF ELASTICITY

FIELD OF THE INVENTION

The invention concerns a method for determination of an irreversible stretch and of a dynamic modulus of elasticity from a paper web. The invention also concerns a method for the control of a papermaking process.

BACKGROUND OF THE INVENTION

It is known from the prior art that, in manufacture of paper and board material, it is necessary to monitor the properties of the web material during the process of manufacture. For the quality control, a number of prior-art on-line or off-line methods are available. As a result of a determination of the properties of the web material, it is possible to regulate different parameters that are used in papermaking. The aim of the regulation is a final product of optimal quality and good runnability of the machines.

Earlier, the significance of the cross-direction tension profile of a paper web both for the quality of the ultimate product and for the runnability of the machines has been realized. In the applicant's FI Patent No. 94,066, there is a thorough discussion of the significance of the tension profile for the smooth running of the process of manufacture and for the quality of the ultimate product.

In the applicant's FI Patent No. 80,522, a method and an equipment for measurement of the tension of a web are described. In said solution, the tension of the web is measured by, in the vicinity of the moving web, fitting a measurement rib, which has a face that is curved in the running direction of the web and in which rib there are pressure metering detectors placed in holes. An air cushion is formed between the moving web and the curved face, in which cushion the air pressure is directly proportional to the tension of the web. The tension of the web is measured indirectly by metering the pressure in the air cushion.

In the FI Patent No. 62,419, a method for measurement of a tension profile is described, which method is based on the speed of propagation of a plane wave. In this method, an acoustic impulse is produced in the web, and the travel time of the impulse is measured by means of a microphone.

In the U.S. Pat. Nos. 2,755,032 and 3,057,574, mechanical and pneumatic equipments of measurement and regulation have been suggested for measurement of the tension profile of a web. In these apparatuses, the web is pressed by means of two shoes, which produce a change in the running direction of the web, and, at the same time, a force directly proportional to the tension of the web is applied to the shoes.

Even though a number of on-line methods are available for examination of the tension profile and of other properties of a web material, it has been difficult to determine the irreversible stretch and the dynamic modulus of elasticity during the process. As a rule, these quantities are determined under laboratory conditions. For this purpose, separate samples must be taken from the web material, and the result of determination of the quantities is obtained only after a delay. Thus, it takes a great deal of time before the necessary adjustments in the process can be made on the basis of the results obtained from the laboratory.

The problems stated above and involved in the prior art have constituted a reason for the present invention.

OBJECTS AND SUMMARY OF THE INVENTION

The object of the present invention is to provide a novel method for determination of an irreversible stretch and of a dynamic modulus of elasticity from a paper web. The aim of the method in accordance with the method is to provide a possibility for rapid adjustment of the regulation parameters employed in the manufacture of paper after determination of the quantities concerned.

In view of achieving the objectives stated above and those that will come out later, the method in accordance with the invention for determination of an irreversible stretch and of a dynamic modulus of elasticity from a paper web is mainly characterized in that the method comprises the following steps:

- the paper web is subjected to an on-line measurement of its cross-direction tension profile at two or more different tension levels,
- a curve is fitted to the number of points of tension measurement carried out at each location of measurement in the cross direction of the paper web,
- the irreversible stretch is determined from each fitted curve, and
- the dynamic modulus of elasticity is determined from each fitted curve.

The method in accordance with the invention for the control of a papermaking process is mainly characterized in that, in said method, the method in accordance with the invention for determination of an irreversible stretch and of a dynamic modulus of elasticity from a paper web is employed for regulation of the dynamic modulus of elasticity and/or of the irreversible stretch.

In carrying the method in accordance with the invention into effect, it is possible to use apparatuses of measurement of the cross-direction tension profile of a web which are known from the prior art and which have possibly already been installed in the paper machine. The tension profile is determined across the entire width of the paper web at two or more different tension levels, and the stretch between targets is determined as a measurement of difference in speed.

At each of the different points of measurement of the tension profile, the measurement results of a number of measured tension profiles are fitted together. From the fitted result thus formed, it is possible to determine the irreversible stretch and the modulus of elasticity of the paper web.

A particular advantage of the present invention is the rapidity of the method of measurement as well as the possibility of integrating the measurement procedure on-line in the rest of the control system of the paper machine.

BRIEF DESCRIPTION OF THE DRAWINGS

In the following, the invention will be described in detail with reference to the exemplifying embodiments of the invention illustrated in the figures in the accompanying drawing, the invention being, however, not supposed to be confined to said embodiments alone.

DETAILED DESCRIPTION OF THE INVENTION

Figure 1:
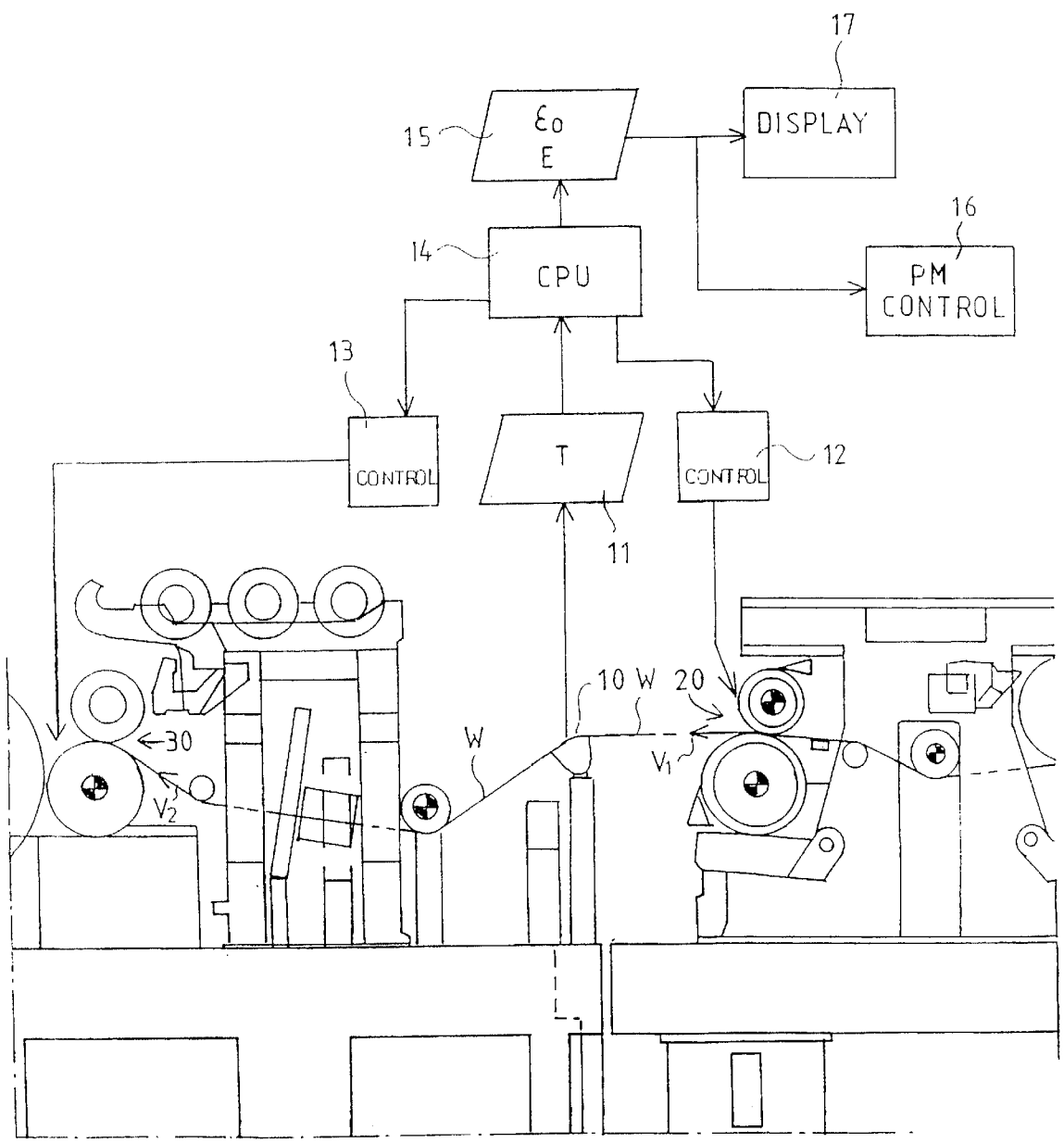
FIG. 1 illustrates a location of an apparatus for measurement of tension profile in a paper machine.

FIG. 1 shows a typical location of an apparatus 10 for measurement of the tension profile in a paper machine. In this exemplifying embodiment, the measurement apparatus has been fitted in the dry end of the paper machine between a calender 20 and a reel-up 30. The measurement data 1 concerning the tension profile are passed along a bus to a data processing equipment 14. The tension profile is measured at different tension levels so that the stretch of the paper web W between the calender 20 and the reel-up 30 is adjusted. A change in the stretch is produced so that the web W speeds in the calender nip and in the reeling nip are altered. In this way, a difference in speed is produced between the calender and the reel-up. The relative stretch $\epsilon$ that was present when each tension profile was measured is determined from the formula:

$$\varepsilon = \frac{v_2 - v_1}{v_1}$$

wherein $v_1$=web speed in the calender nip $v_2$=web speed in the reeling nip.

The data processing equipment 14 gives commands concerning the regulation of the different speeds to the regulation units 12 and 13 for the drives whose speeds can be regulated. The regulation unit 12 controls the calender nip, and the regulation unit 13 controls the reeling nip. After the desired tension profiles have been measured at a number of, preferably three, different tension levels, the data processing equipment 14 computes the profiles 15 of irreversible stretch and of dynamic modulus of elasticity by means of the fitting method that will be described later. These profiles can be displayed in a display apparatus 17, which can be, e.g., a display monitor or a printer. The profiles 15 are used for making the regulations of the papermaking process by means of the control unit 16 of the paper machine. The control unit 16 can be based on automatic feedback regulation and/or on manual regulation.

Figure 2:
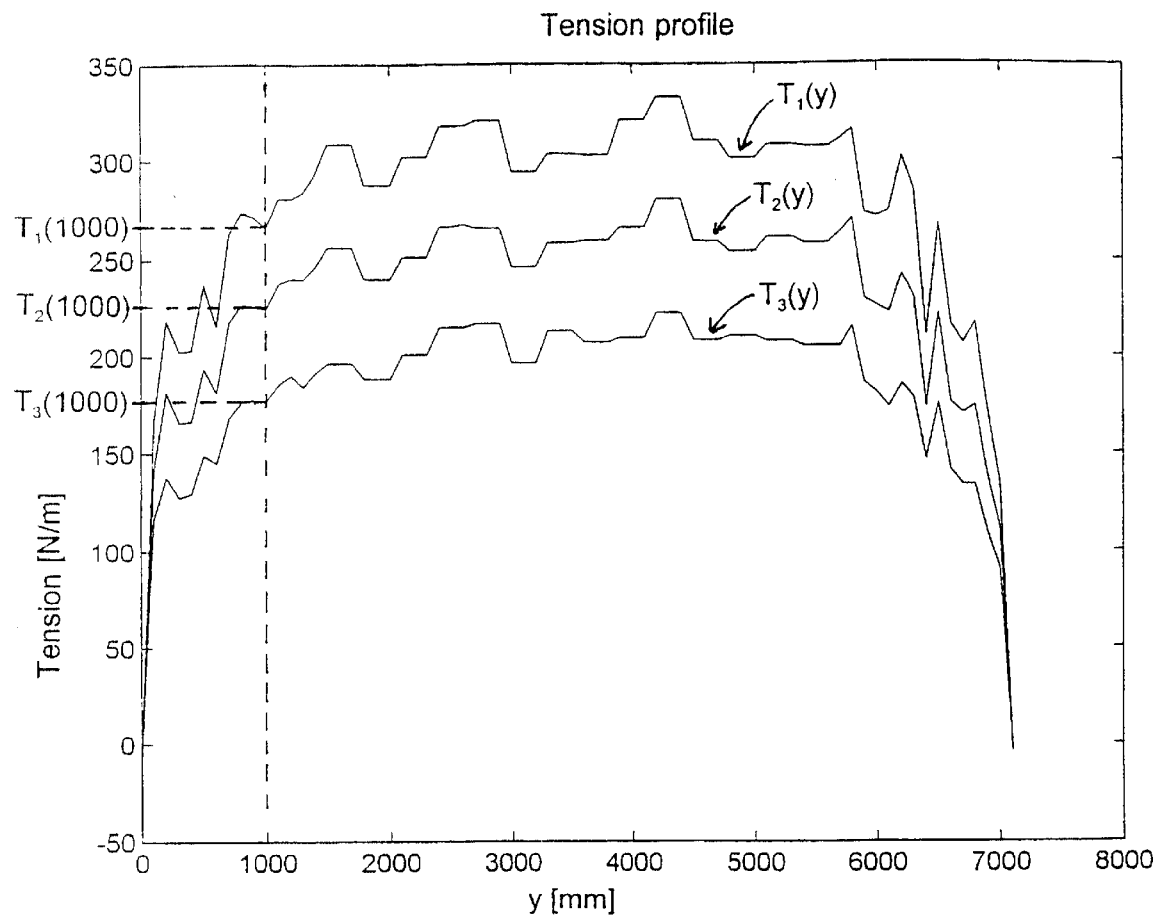
FIG. 2 illustrates a result of measurement of a tension profile at three different levels of tension.

FIG. 2 shows a measurement result obtained by means of the apparatus 10 for measurement of the tension profile, wherein the tension profile has been measured at three different known tension levels $T_1(y)$, $T_2(y)$ and $T_3(y)$, which levels correspond to the values of relative stretch $\epsilon_1$, $\epsilon_2$ and $\epsilon_3$. In the figure, the vertical axis represents the tension as the units N/m (newtons per metre). The horizontal axis represents the location y in the cross direction of the paper web, the unit being mm (millimetre). In this example, the width of the paper web is 7 meters. In FIG. 2, as an example, the tension values $T_1(1000)$, $T_2(1000)$ and $T_3(1000)$ corresponding to a cross-direction distance of 1000 mm of the paper web have been indicated in respect of each graph of tension profile $T_1(y)$, $T_2(y)$ and $T_3(y)$.

Figure 3:
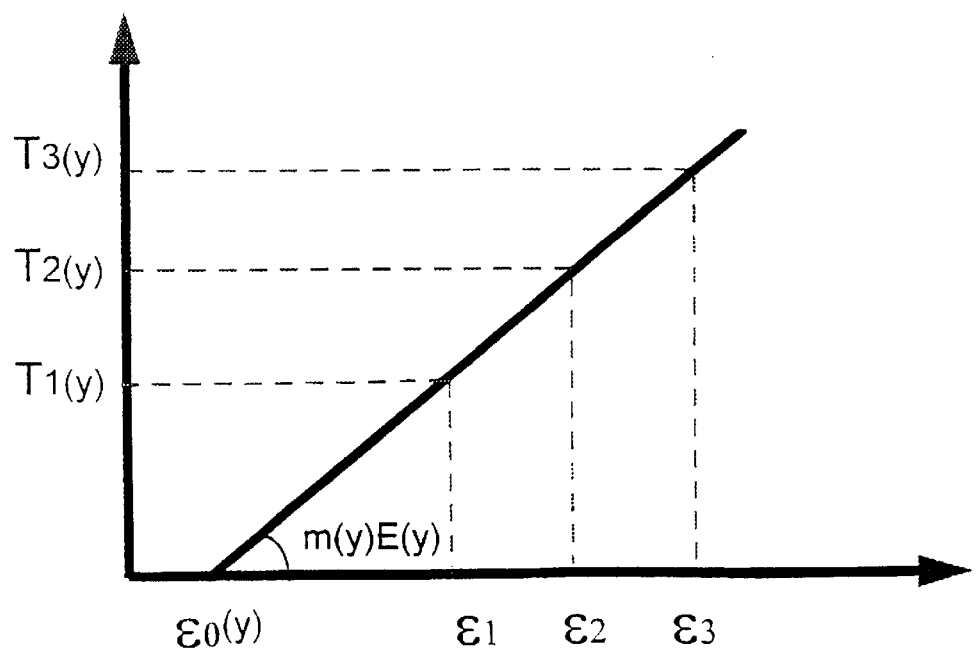
FIG. 3 illustrates the principle of fitting together of measurement points.

FIG. 3 illustrates the principle with which the tension values measured with each stretch value $\epsilon_1$, $\epsilon_2$ and $\epsilon_3$ are fitted in the curve. This fitting is carried out at each point of measurement of the tension profile. The fitting of a straight line at the measurement points is carried out, for example, by making use of the method of fitting of the least squares. The equation of the straight line drawn in FIG. 3 has the following form:

$$T(y) = m(y)E(y)(\epsilon - \epsilon_0)^n$$

wherein $T(y) = T_1(y)$, $T_2(y)$, $T_3(y)$=tension profile [N/m]

$m(y)$=basis weight profile [kg/sq.m]

$E(y)$=dynamic modulus of elasticity [sq.m/s$^2$]

$\epsilon = \epsilon_1$, $\epsilon_2$ and $\epsilon_3$=relative stretch $\epsilon_0$=irreversible stretch $n \approx 1$ By means of the straight line fitted on the measurement results, illustrated in FIG. 3, it is possible to determine the irreversible stretch $\epsilon_0$ from the measurement results, which irreversible stretch is obtained from the intersection point of the straight line on the horizontal axis. The angle coefficient of the straight line corresponds to the dynamic modulus of elasticity $E(y)$ of the measurement point.

Figure 4:
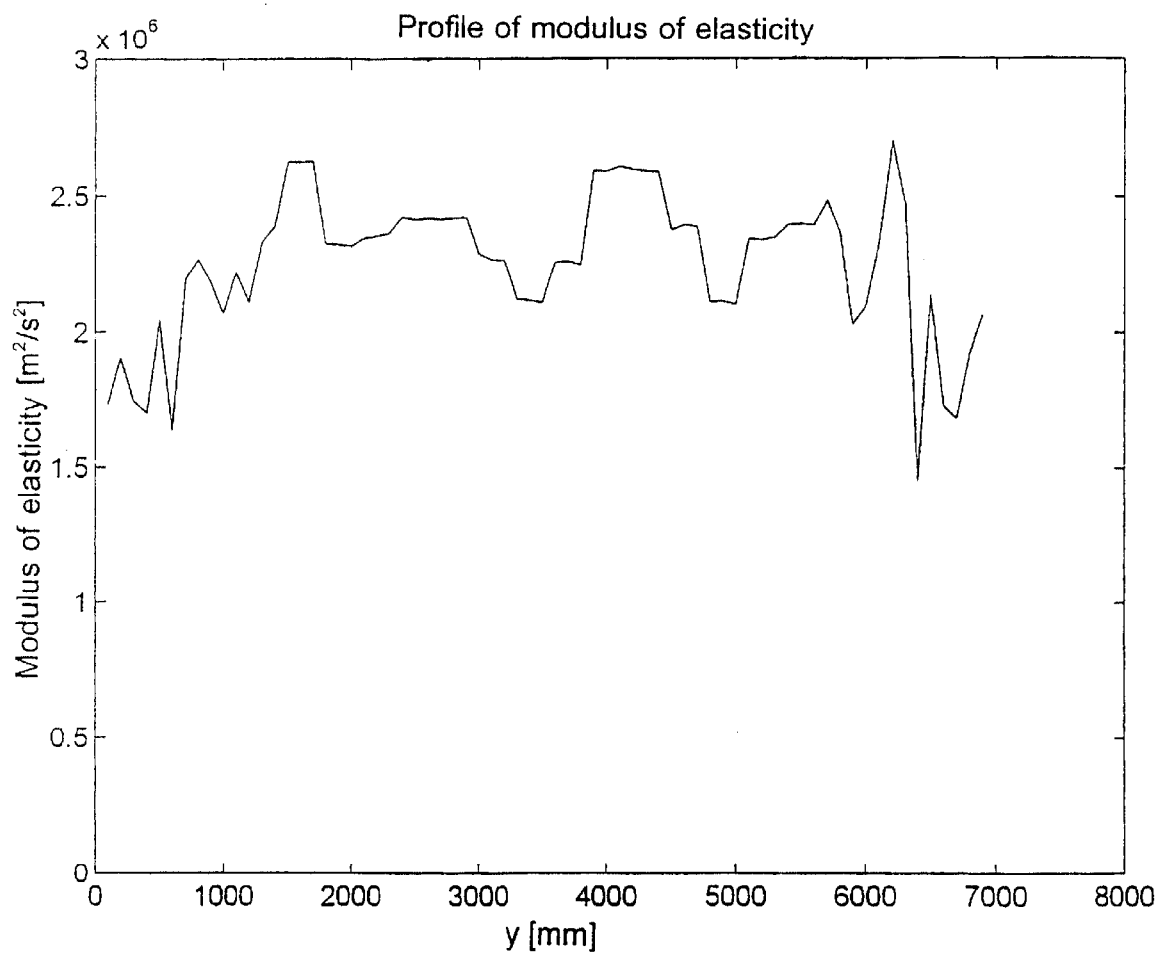
FIG. 4 illustrates a profile of modulus of elasticity of a paper web.

FIG. 4 shows the CD profile of the dynamic modulus of elasticity E of the paper web determined in the way described above. In the figure, the vertical axis represents the elasticity module E, whose unit is sq.m/s$^2$, and the horizontal axis represents the location on the paper web W in the CD direction.

Figure 5:
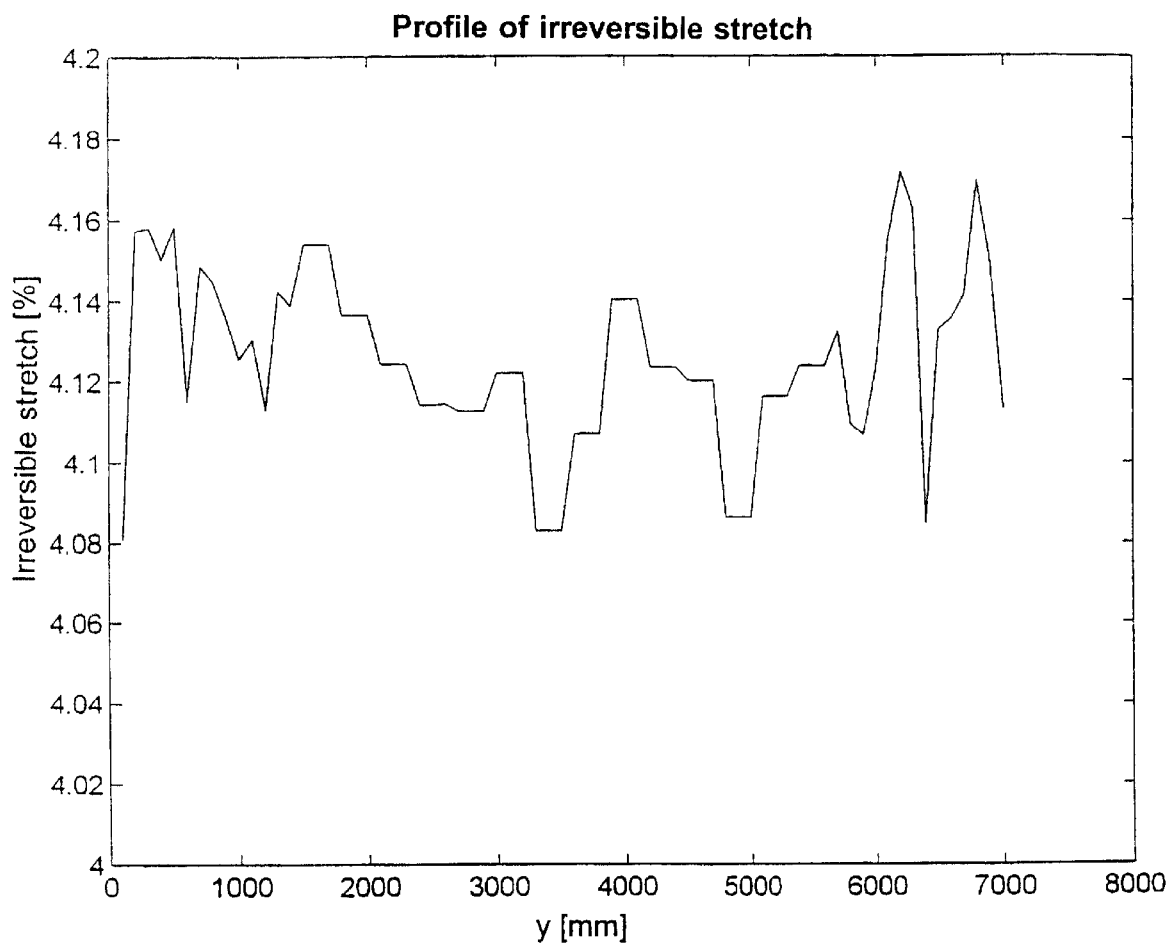
FIG. 5 illustrates a profile of irreversible stretch of a paper web.

FIG. 5 shows the profile of the irreversible stretch $\epsilon_0$ of the paper web W determined in the way described above. In the figure, the vertical axis represents the irreversible stretch $\epsilon_0$ as a percentage, and the horizontal axis represents the location in the cross-direction of the paper web W.

Above, an exemplifying embodiment has been described, according to which the measurement of the tension profile is carried out between a calender and a reel-up, i.e. in the dry end of the paper machine. The method can also be applied to other parts of a paper machine. Possible other locations of measurement are, for example, the press section, a coating machine, and an off-line calender. In such a case, the determination of the quantities differs to some extent from what has been stated above, because the stretch/tension conduct of the paper depends on the degree of dryness of the paper.

In the following, the patent claims will be given, and the different details of the invention may show variation within the scope of the inventive idea defined in said claims and differ from what has been stated above by way of example only.

What is claimed is:

1. A method for determination of an irreversible stretch and of a dynamic modulus of elasticity from a paper web for control of a papermaking process, wherein the method comprising the steps of measuring an on-line cross-direction tension profile, of the paper web (W) at two or more different tension levels, developing a fitted curve to the number of points of tension measurement carried out at each location of measurement in the cross direction of the paper web (W) of said adjusting step said curve describing local paper web tension as a function of relative stretch, determining an irreversible stretch ($\epsilon_0$) from each fitted curve, and determining a dynamic modulus of elasticity (E) from each fitted curve, wherein the determined values and profiles of irreversible stretch ($\epsilon_0$) and dynamic modulus of elasticity (E) are used for the control of the papermaking process; and wherein the control of the papermaking process is carried out as on-line feedback control by means of an automation system so that set values: or certain target areas or target values are assigned to said levels and/or profiles of irreversible stretch ($\epsilon_0$) and dynamic modulus of elasticity.

2. A method as claimed in claim further comprising the step of:

controlling the levels of tension of the paper web (W) by means of a web (W) speed difference ($V_2-V_1$).

3. A method as claimed in claim 1, wherein the measurement of the tension profile is carried out in a dry end of the paper machine.

4. A method as claimed in claim 1, wherein the measurement of the tension profile is carried out on a run of the web (W) between an on-line calender (20) and a reel-up (30).

5. A method as claimed in claim 1, wherein the measurement of the tension profile is carried out in a press section.

6. A method as claimed in claim 1, wherein the measurement of the tension, profile is carried out in a coating machine.

7. A method as claimed in claim 1, wherein the measurement of the tension profile is carried out in an off-line calender.

8. A method as claimed in claim 1, wherein at least one of the profiles of irreversible stretch ($\epsilon_0$) and dynamic modulus of elasticity (E) are affected by means of at least one of the following parameters and devices of the papermaking process: devices for regulation of basis weight, moisture content add thickness, slice spindles and dilution valves of the headbox, steam box in the press section and wire loads in nips, moistening device, wire loads and/or steam boxes in a calender.

* * * * *